(12) United States Patent
Roshi et al.

(10) Patent No.: US 9,095,259 B2
(45) Date of Patent: Aug. 4, 2015

(54) METHOD AND SYSTEM FOR HIGH RESOLUTION NUTATED SLICE RECONSTRUCTION USING QUARTER DETECTOR OFFSET

(75) Inventors: Aleksander Roshi, Medford, MA (US); Basak Ulker Karbeyaz, Medford, MA (US); David Rozas, Medford, MA (US)

(73) Assignee: Analogic Corporation, Peabody, MA (US)

( * ) Notice: Subject to any disclaimer, the term of this patent is extended or adjusted under 35 U.S.C. 154(b) by 386 days.

(21) Appl. No.: 13/508,859

(22) PCT Filed: Dec. 4, 2009

(86) PCT No.: PCT/US2009/066760
§ 371 (c)(1),
(2), (4) Date: Aug. 7, 2012

(87) PCT Pub. No.: WO2011/068515
PCT Pub. Date: Jun. 9, 2011

(65) Prior Publication Data
US 2012/0294415 A1    Nov. 22, 2012

(51) Int. Cl.
*A61B 6/00* (2006.01)
*A61B 6/03* (2006.01)
*G06T 11/00* (2006.01)

(52) U.S. Cl.
CPC .............. *A61B 6/032* (2013.01); *G06T 11/006* (2013.01); *A61B 6/4021* (2013.01); *G06T 2211/421* (2013.01)

(58) Field of Classification Search
CPC ............ G06T 11/006; G06T 2211/421; G06T 2211/40; G06T 2211/00; A61B 6/4021

USPC .............................................. 378/4–20, 901
See application file for complete search history.

(56) References Cited

PUBLICATIONS

Flohr et al. Image Reconstruction and Image Quality Evaluation for a 16 Slice CT Scanner, Medical Physics30:832-845 (2003).*
Schöndube et al., "Accurate Helical Cone-Beam CT Reconstruction with Redundant Data," Physics in Medicine and Biology, 54:4625-4644 (2009).

(Continued)

*Primary Examiner* — Courtney Thomas
(74) *Attorney, Agent, or Firm* — McDermott Will & Emery LLP

(57) ABSTRACT

A method and system are provided for generating high resolution CT images. The NSR# method improves on the AMPR method, by increasing the in-plane image resolution of CT scanners, in the helical scanning mode. The provided method uses the quarter detector offset and interleaving of complementary data to achieve in plane image resolution that is similar to the high resolution axial scanning mode utilizing quarter detector offset and interleaving. The method includes several ways of choosing the data to be interleaved, like NSR# with two planes, NSR# with 3 planes, NSR# with multiple planes. The interleaved data are used to create high resolution tilted slices. The NSR# method optimizes the untilting filter to create a mix of high and low resolution tilted slices to achieve the desired in-plane image resolution-image artifact balance required for the imaging task. In one embodiment in the untilting process one may use only high resolution tilted slices, for maximum resolution benefit. In another embodiment one may mix high resolution tilted slices with standard resolution tilted slices resulting from data that did not go through interleaving. This creates unfilled slices of higher resolution than the standard and with lower artifacts. In another embodiment for scans with pitch lower than ⅔ one may reduce the collimation to reduce the dose to the patient.

15 Claims, 18 Drawing Sheets

(56) References Cited

PUBLICATIONS

Stierstorfer et al., "Segmented Multiple Plane Reconstruction: A Novel Approximate Reconstruction Scheme for Multi-Slice Spiral CT," Physics in Medicine and Biology, 47:2571-2581 (2002).

Chen et al., "General Surface Reconstruction for Cone-Beam Multislice Spiral Computed Tomography," Medical Physics, 30:2804-2821 (2003).

Stierstorfer et al., "Image Reconstruction and Image Quality Evaluation for a 16-Slice CT Scanner," Medical Physics, 30:832-845 (2003).

Flohr et al., "Image Reconstruction and Image Quality Evaluation for a 16-Slice CT Scanner," Medical Physics, 30:832-845 (2003).

Schondube et al., "Accurate Helical Cone-Beam CT Reconstruction with Redundant Data," Physics in Medicine and Biology, 54:4626-4644 (2009).

International Search Report and the Written Opinion from corresponding PCT Application No. PCT/US2009/066760 dated Aug. 9, 2010.

\* cited by examiner

METHOD AND SYSTEM FOR HIGH RESOLUTION NUTATED SLICE RECONSTRUCTION USING QUARTER DETECTOR OFFSET

FIELD OF THE DISCLOSURE

The present disclosure relates generally to computed tomography, and more particularly to a method and system for providing high resolution nutated slice reconstruction using a quarter detector offset.

BACKGROUND OF THE DISCLOSURE

Nutated slice reconstruction (NSR)-type algorithms are described in U.S. Pat. No. 5,802,134, Larson et al., "Nutating slice CT image reconstruction apparatus and method," 1999 ("Larson"); U.S. Pat. No. 7,215,805 B2, Bruder et al., "Method and apparatus for spiral scan computed tomography," 2007 ("Bruder"); S. Schaller, K. Stierstorfer, H. Bruder, M. Kachelrietβ, and T. Flohr, "Novel approximate approach for high-quality image reconstruction in helical cone beam CT at arbitrary pitch", Proc. SPIE vol. 4322, p. 113-127, 2001 ("Schaller"); and U.S. Pat. No. 7,027,552 B2, "High resolution CT scanner," 2006 ("Shechter"). As described these nutated slice-type algorithms are approximate algorithms used to reconstruct helical scan data from multi-row CT scanners. The algorithms interpolate multi-row data into slices (planes) which have normals that are tilted with respect to the gantry rotation axis. The angle of the tilted planes is chosen to fit the helical path of the x-ray source in order to reduce artifacts. These tilted slices are then reconstructed using 2D filtered backprojection techniques, followed by interpolation in the direction of the rotation axis ("untilting") to produce images perpendicular to the rotation axis.

Each tilted slice touches the helical trajectory of the x-ray source at a locus called "attachment point." The original NSR algorithm described by Larson uses a single tilted plane at each attachment point which was suitable for higher helical pitch applications. This concept was extended in the Adaptive Multiple Plane Reconstruction ("AMPR") algorithm described in Bruder and Schaller. The AMPR algorithm uses multiple tilted planes at each attachment point to improve dose utilization for lower pitches. In CT scanners with an x-ray focal spot which is fixed with respect to the rotating detector array, the NSR and AMPR algorithms use of half-scan reconstruction approach results in the in-plane sampling rate of 1/wdiso near isocenter, where wdiso is the in-plane pitch of the detector at isocenter. This sampling rate limits the resolution of the reconstructed images. This type of focal spot shall be henceforth referred to as "fixed focal spot.". One approach to improve the resolution of CT scanner in an axial scanning mode is to use interleaving of rays which are 180 degrees apart and offset by a quarter detector, as described in U.S. Pat. No. 4,051,379 Zacher, Jr. "Axial tomography apparatus and detector" 1977 ("Zacher, Jr."). Another approach to improve the resolution of a CT scanner in helical and axial scanning modes is to increase the in-plane sampling rate by using an x-ray source with a "flying focal spot," as described in U.S. Pat. No. 6,256,369 Lai, "Computerized tomography scanner with longitudinal flying focal spot" 2001 ("Lai") which may be more expensive than a fixed focal spot source.

SUMMARY OF THE DISCLOSURE

An improved system and method are provided in which an alternative reconstruction technique is used to increase the in-plane sampling rate and improve reconstructed image resolution without requiring "flying focal spot" hardware.

In one embodiment a helical CT scanner for scanning an object is provided. The scanner comprises: an x-ray source constructed so as to define a focal spot, and a detector array comprising a plurality of detectors positioned to rotate with the source about an axis of rotation, wherein the source and detector array are arranged to rotate about a rotation axis with the object moving relative to and between the source and detector array in a direction parallel to the rotation axis during a helical scan; and a processor constructed and arranged so as to process data acquired by the detector array during the helical scan so as to represent reconstructed tilted slices with respect to the rotation axis; wherein data representing the tilted slices is used to interpolate untilted images in planes perpendicular to the rotation axis. The x-ray source is constructed so as to define a fixed focal spot during the helical scan, and the detectors of the array are positioned relative to the source and the center of rotation (the "isocenter" of the scanner) during rotation so as to provide a quarter detector offset so that rays from 180° apart during rotation can be interleaved.

In another embodiment a method is provided for generating a high resolution nutated slice reconstructed image of an object with a CT scanner comprising a x-ray source constructed so as to define a fixed focal spot, and a detector array comprising a plurality of detectors positioned to rotate with the source about an axis of rotation and arranged to as to provide a quarter detector offset, wherein the source and detector array are arranged to rotate about a rotation axis with the object moving relative to and between the source and detector array in a direction parallel to the rotation axis during a helical scan. The exemplary method comprises: scanning the object so as to generate helical cone beam scan projection data of the object using a fixed focal spot; interpolate the cone beam projection data to create data that represent complementary tilted plane projection data to be interleaved; interleaving complementary tilted planar projection data resulting from complementary plane sets and offset by a quarter detector; filtering with a kernel and reconstructing the interleaved projection data for each of the planes so as to create high resolution tilted images; interpolating data from the tilted images so as to create data representing untilted images in planes perpendicular to the rotation axis.

In still another embodiment a method is provided for generating a high resolution nutated slice reconstructed image of an object with a CT scanner comprising a x-ray source constructed so as to define a fixed focal spot, and a detector array comprising a plurality of detectors positioned to rotate with the source about an axis of rotation and arranged to as to provide a quarter detector offset, wherein the source and detector array are arranged to rotate about a rotation axis with the object moving relative to and between the source and detector array in a direction parallel to the rotation axis during a helical scan. The method comprises: scanning the object so as to generate helical cone beam scan projection data of the object using a fixed focal spot; interpolating the cone beam projection data to create data that represent complementary tilted plane projection data to be interleaved; interleaving complementary tilted plane projections resulting from complementary plane sets and offset by quarter detector; filtering with a kernel and reconstruct the interleaved projection data for each of the planes so as to create high resolution tilted images; interpolating the cone beam projection data to create data that represent tilted plane projection data for non-interleaving, standard resolution planes; filtering with a separate kernel and reconstructing non-interleaved projection data for certain planes so as to create lower artifact tilted images; interpolating data from the high resolution and standard resolution tilted images so as to create data representing image planes perpendicular to the rotation axis.

GENERAL DESCRIPTION OF THE DRAWINGS

The drawing figures depict preferred embodiments by way of example, not by way of limitations. In the figures, like reference numerals refer to the same or similar elements.

Referring to the drawings.

DETAILED DESCRIPTION OF THE DRAWINGS

A system and method are disclosed which increases the in-plane image resolution for a helical multi-row CT scanner without using a "flying focal spot in x" x-ray source. This is accomplished by utilizing quarter detector offset (QDO) geometry, wherein data is collected from the detectors that are displaced one-half a detector width with respect to the rays from the X-ray source during each view every 180° of rotation. In this way the projection data that are interleaved before reconstruction will have increased sampling in x-direction, resulting into higher in-plane resolution images.

Figure 1:
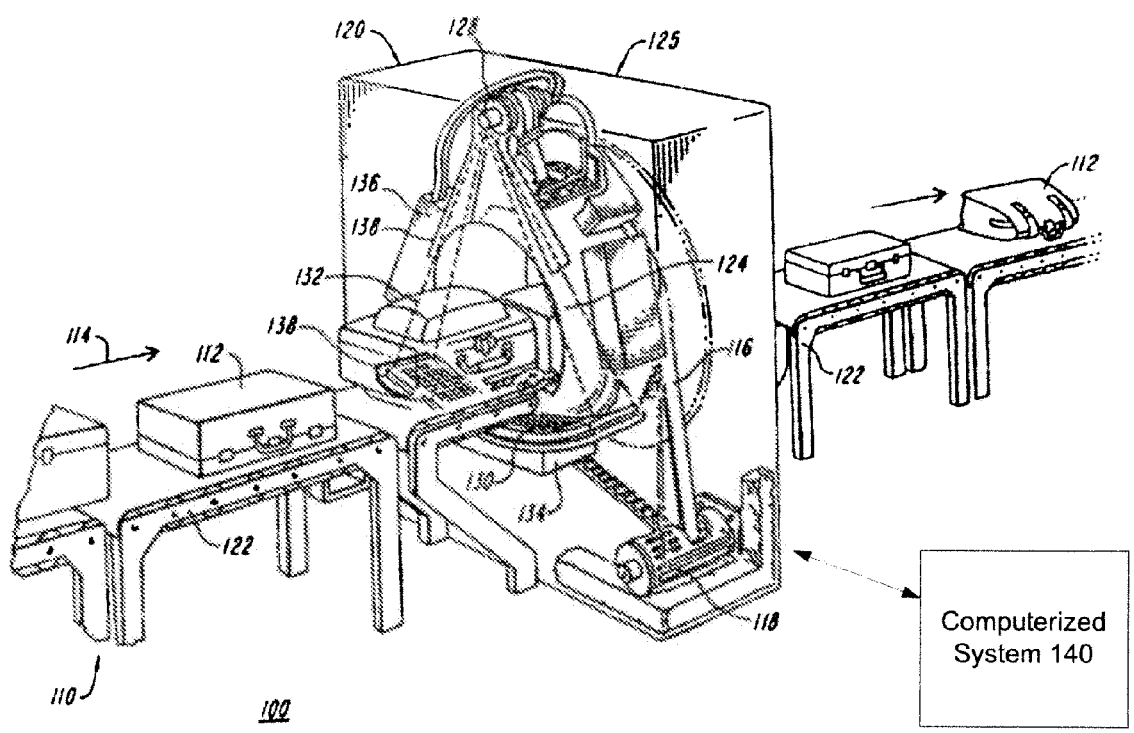
FIG. 1 is a perspective view of a typical baggage scanning system.
Figure 2:
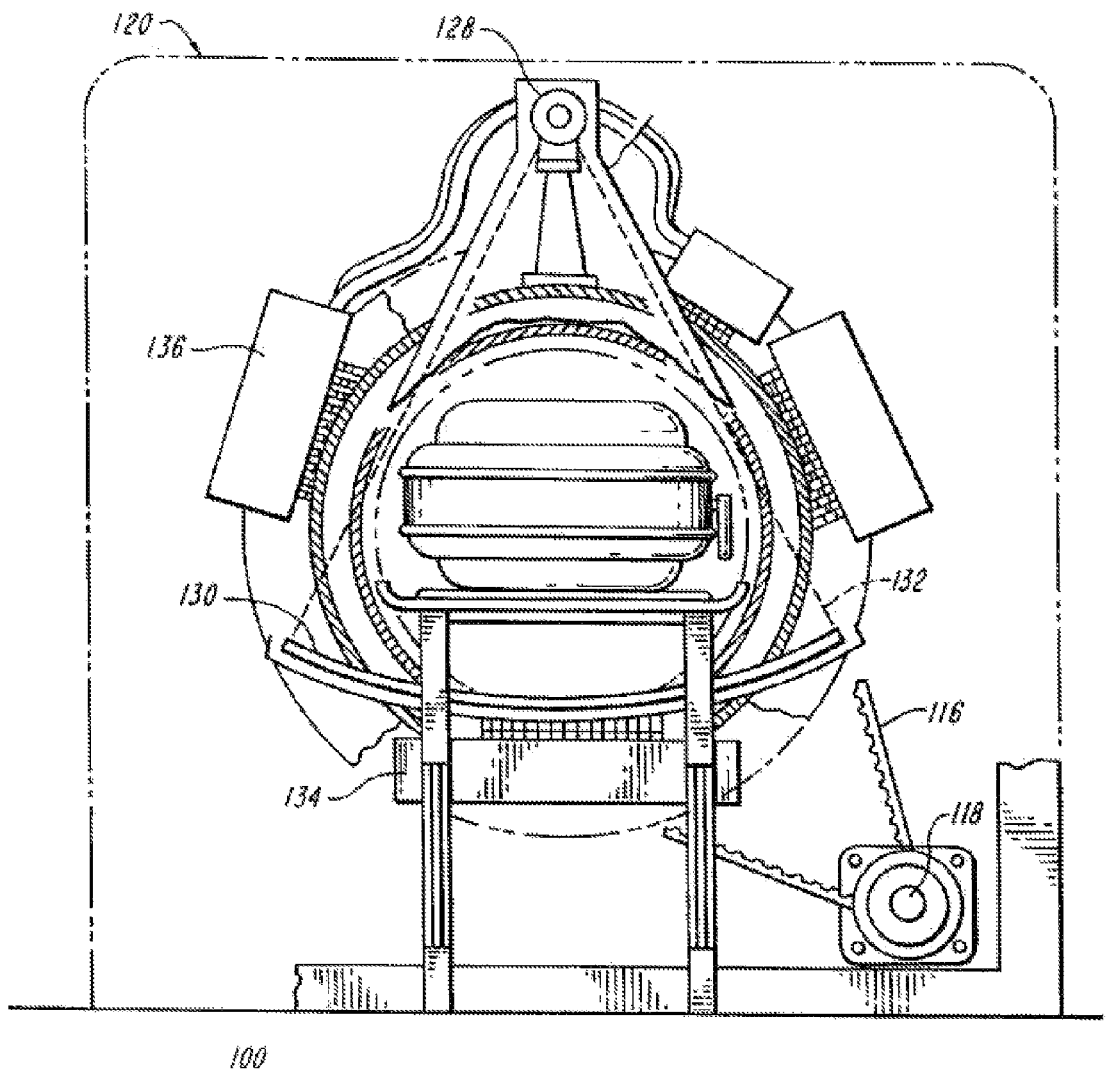
FIG. 2 is a cross-sectional end view of the system of FIG. 1.
Figure 3:
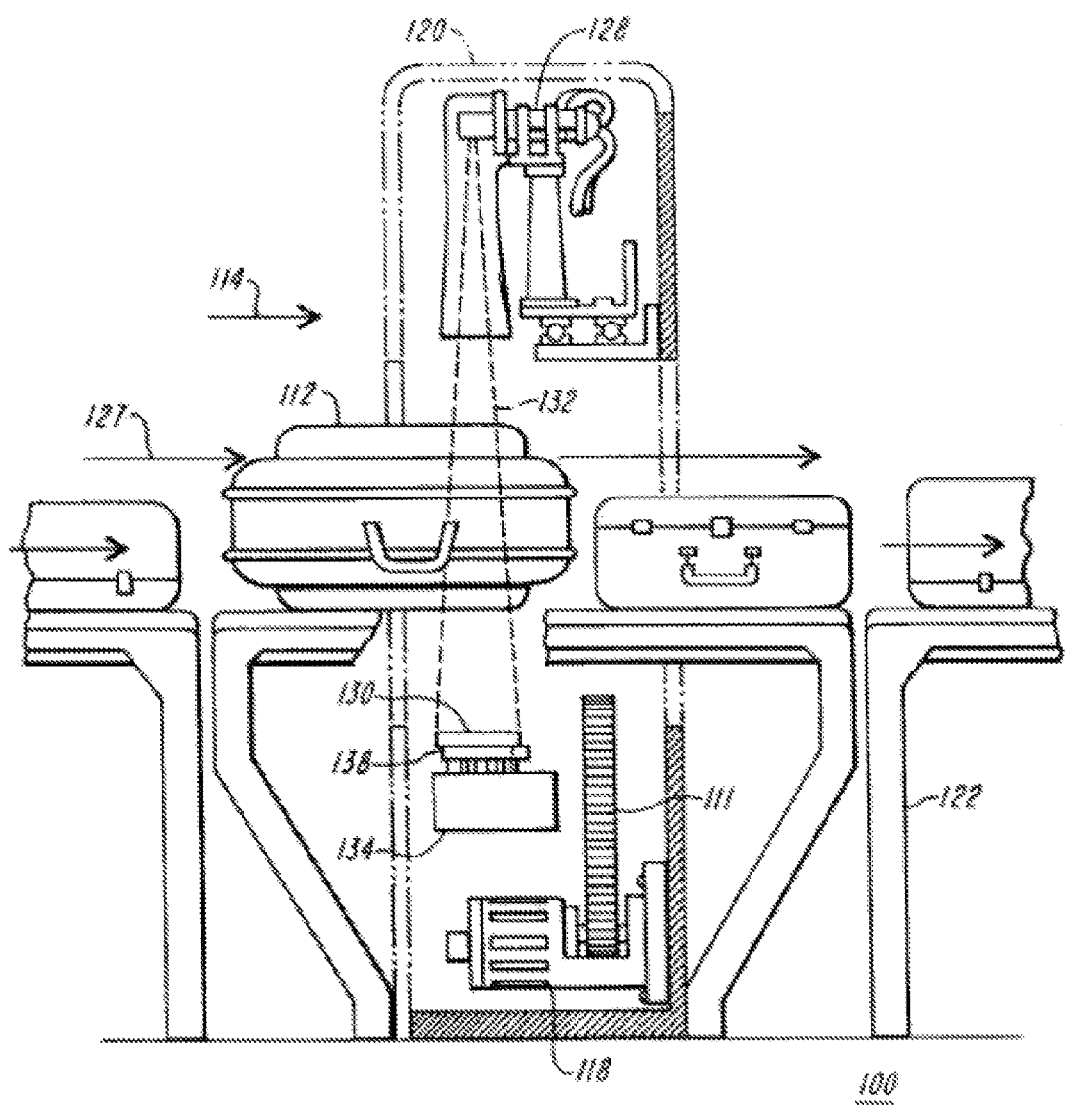
FIG. 3 is a cross-sectional radial view of the system of FIG. 1.

An example of a helical multi-row CT scanner is illustrated in FIGS. 1-3. The system 120 includes an X-ray tube 128 and a detector array 130 which are disposed on diametrically opposite sides of the platform 124. The detector array 130 is preferably a two-dimensional array of any arbitrary geometry, as will be explained more fully hereinafter. The system 120 further includes a data acquisition system (DAS) 134 for receiving and processing signals generated by detector array 130, and an X-ray tube control system 136 for supplying power to, and otherwise controlling the operation of X-ray tube 128. The system 120 is also preferably provided with a computerized system (shown in FIG. 1 at 140) for processing the output of the data acquisition system 134 and for generating the necessary signals for operating and controlling the system 120. The computerized system 140 can also include a monitor for displaying information including generated images. System 120 also includes shields 138, which may be fabricated from lead, for example, for preventing radiation from propagating beyond gantry 125.

The X-ray tube 128 includes at least one cathode and one anode for creating at least one separate focal spot from which an X-ray beam can be created and generated. The beam shown generally at 132 in FIGS. 1-3, passes through a three dimensional imaging field, through which conveying system 110 transports baggage 112. After passing through the baggage disposed in the imaging field, detector array 130 can receive each beam 132. The detector array then generates signals representative of the densities of exposed portions of baggage 112. The beams 132 therefore define a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles. The data acquisition system 134 includes a processor subsystem within system 140 for carrying out the data processing described herein.

Figure 4:
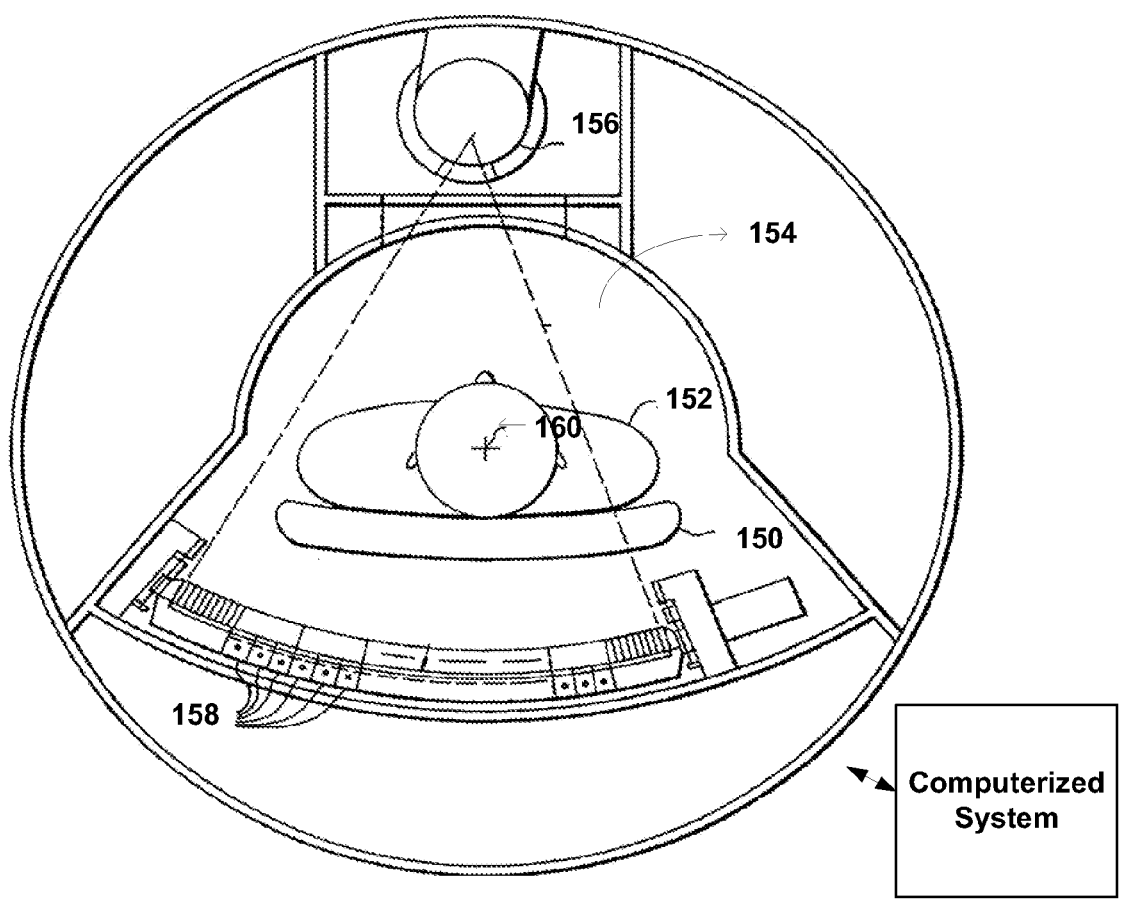
FIG. 4 is a cross-sectional end view of a typical medical scanner.

While the FIGS. 1-3 illustrate a helical CT scanner used as a baggage scanner, the presently described system and method can be applied to any helical CT scanner for any application including medical scanning such as shown in FIG. 4, wherein a patient pallet 150 is used to move the patient 152 in an axial direction through the aperture 154 during rotation of the x-ray source 156 and detector array 158 about the rotation axis 160.

For purposes of explanation, a right handed stationary frame of reference, $X_s$, $Y_s$, $Z_s$, is attached with the scanner, and a right handed rotating frame of reference X, Y, Z, rotates about the $Z_s$ axis so that the rotating Y axis is attached to the rotating x-ray focal spot, the Z axis is the same with the stationary $Z_s$ axis, and the X axis is perpendicular to both Y and Z, so that it forms a right handed frame of reference.

In order to process the data, the system and method utilizes an algorithm referred to hereinafter as "NSR#" (pronounced "NSR-sharp"). The NSR# algorithm interpolates multi-row helical data to create data that lie in planes tilted with respect to the rotating frame of reference with axes X and Y, by angle gamma (γ) with respect to the X-axis, and by angle delta (δ) with respect to the Y-axis. The angles γ and δ are best illustrated by way of example in FIG. 5. The values of δ and γ are predetermined for each tilted slice. The angle γ is determined by the scan pitch and is the same for all tilted planes for a particular implementation. The angle δ is determined by the phase of the slice and the number of planes passing through and including an attachment point. The number of planes passing through and including an attachment point is predetermined for each possible scan pitch allowed for scanning. For purposes of explanation, the number of fan views needed to reconstruct one tilted slice is "N", while "α" is the fan view angle defined with respect to the center view of the set of views needed to reconstruct a tilted plane. The center view is located at an angle $\Theta_i$ with respect to the stationary frame of reference.

Figure 5:
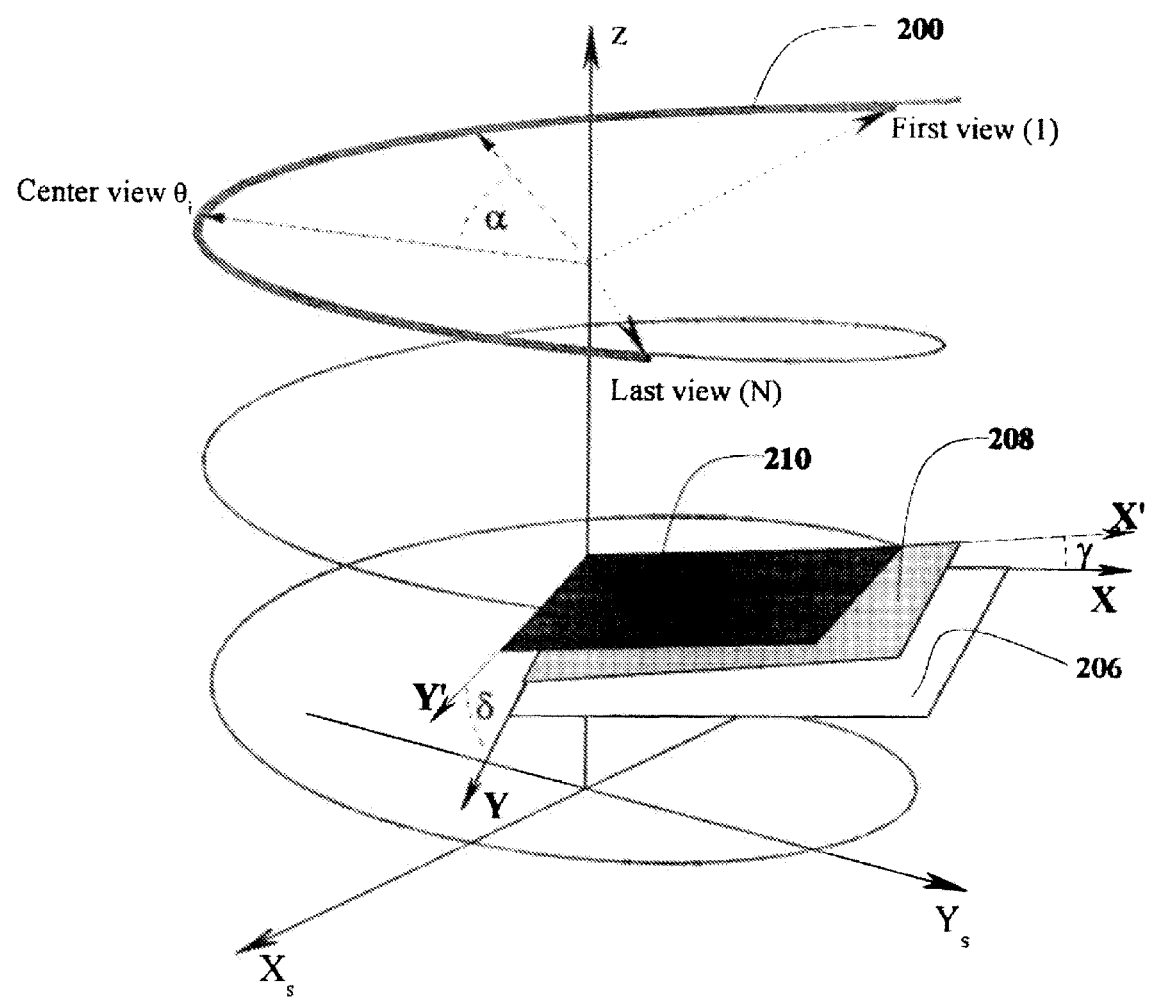
FIGS. 5 and 6 are perspective, spatial illustrations of an example of the development of the relevant tilted planes.
Figure 6:
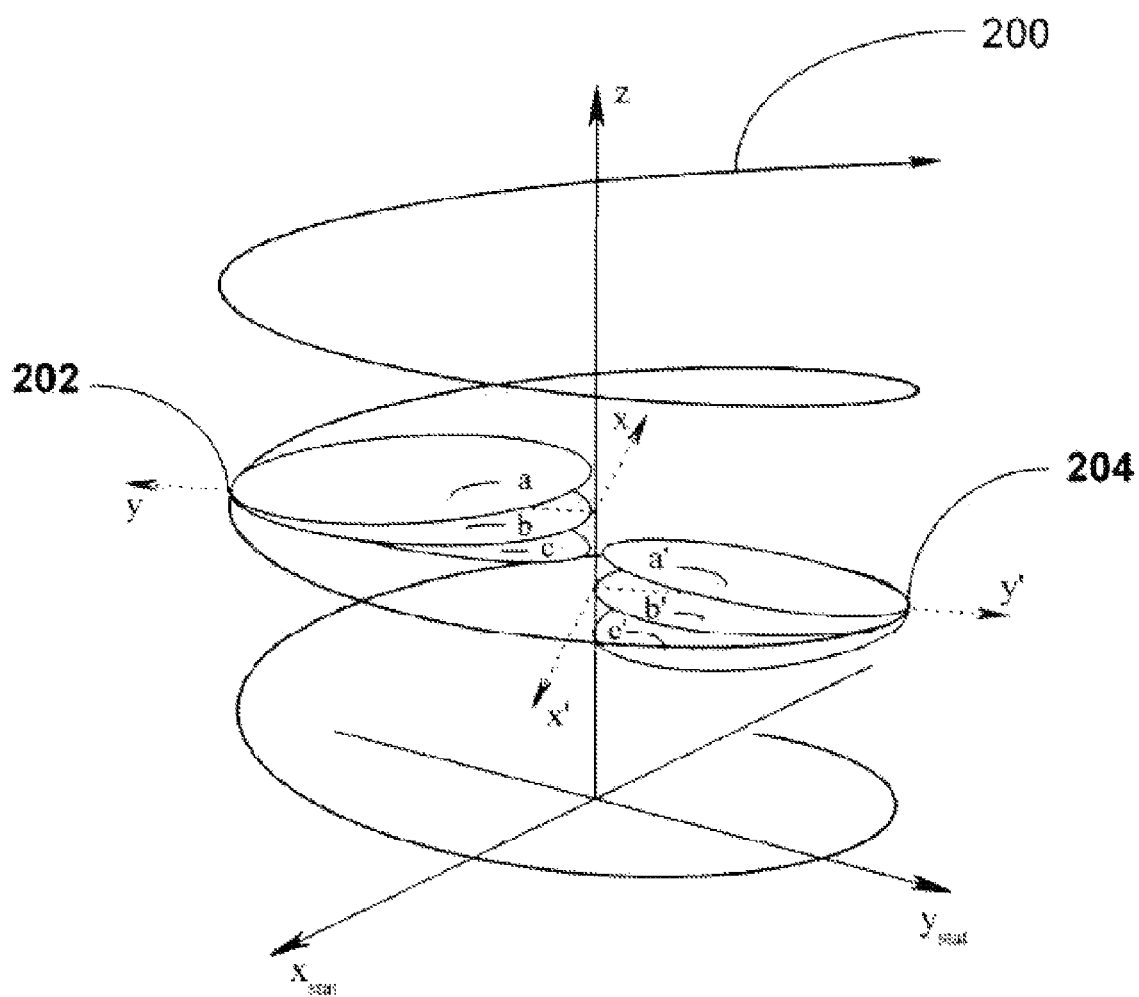

FIG. 6 illustrates an example of two sets of doubly-tilted planes attached to the x-ray source trajectory at attachment points separated by half a rotation. The spiral line 200 in FIGS. 5 and 6 is a typical trajectory of the x-ray source with respect to the object (not shown) being scanned. Helical scan pitch, p, is defined as a ratio of x-ray source displacement along z-axis in a single rotation, divided by the detector collimation size in the z-axis (projected to the isocenter).

In accordance with one aspect of the present invention, as in AMPR, the first tilt angle, γ, is chosen to minimize the distance of the x-ray source to the tilted plane for a center ray over all the views used to reconstruct the slice. In one embodiment, NSR# extends the AMPR algorithm framework by adjusting the second tilt angle δ to allow interleaving of samples which come from two complementary tilted planes that satisfy the following conditions:

(1) The attachment points of those tilted planes (shown by way of example in FIG. 6 at 202 and 204) are separated by half of a rotation of the x-ray source, and (2) The planes intersect along a line which connects the two attachment points.

As illustrated by way of example in FIG. 6, tilted planes a, b and c are attached at location 202 to the x-ray source trajectory 200 half a rotation away from the attachment point 204 for tilted planes a', b' and c'. All planes are tilted by an angle γ with respect to the X axis of the rotating frame of reference, and have varying tilt angle δ with respect to the Y axis of the rotating frame of reference. As illustrated in FIG. 5, the tilted plane 210 is obtained by first starting with a plane 206 perpendicular to the z-axis, rotating the plane to 208 by the angle γ, around the Y axis, followed by a rotation about the X-axis with the angle δ.

The interleaved samples form "combined" slices which have in-plane data sampling rate of 1/(2*wdiso) near the isocenter, where "wdiso" is the in-plane detector pitch at isocenter. The combined slices are then reconstructed using 2D filtered backprojection techniques and "untilted" to images perpendicular to the axis of rotation by interpolating along that axis.

One embodiment of the present invention uses two planes per attachment point, one with tilt angle δ=0 and one with non-zero δ. This arrangement can be used for low helical pitch (e.g., p<⅔) scans. Using the notation shown in FIG. 6, this approach interleaves samples from planes b' and c. In one embodiment, the tilt angles γ for planes b' and c are chosen as follows.

The c plane has a tilt angle γ optimized to reduce the distance of the focal spot to the tilt plane (as in AMPR) and δ=0. The b' plane has the same angle γ, but δ is modified so that the z-coordinates b' and c planes at isocenter are the same. In this embodiment, some of the rows at one side of the detector array may not be utilized. Consequently, in order to avoid overdosing, the collimation may be decreased (which leads to an increase in the helical pitch value for the same table speed).

For higher helical scan pitches (in the example give this occurs when the pitch p≥⅔), at least two alternative embodiments can be utilized. Specifically, one embodiment uses only tilted planes with non-zero δ angles. This embodiment is referred to as "NSR# with 2 planes." Using the notation shown in FIG. 6, this approach interleaves samples from planes c and a', but does not use planes b and b'. In another embodiment, referred to as "NSR# with 3 planes," a plane with a zero δ angle, in addition to the two tilted planes with non-zero δ angles is used. Using the notation shown in FIG. 6, this approach interleaves samples from planes c and a', and uses planes b and b' without interleaving. Since the zero δ angle planes (b and b') are not interleaved, the data in those planes has 1/wdiso in-plane sampling rate near the isocenter.

The images resonstructed in tilted planes are then interpolated ("untilted") to images in planes perpendicular to the axis of rotation 127. Both NSR# with 2 planes and NSR# with 3 planes have higher image resolution compared to prior art NSR and AMPR algorithms.

Figure 7:
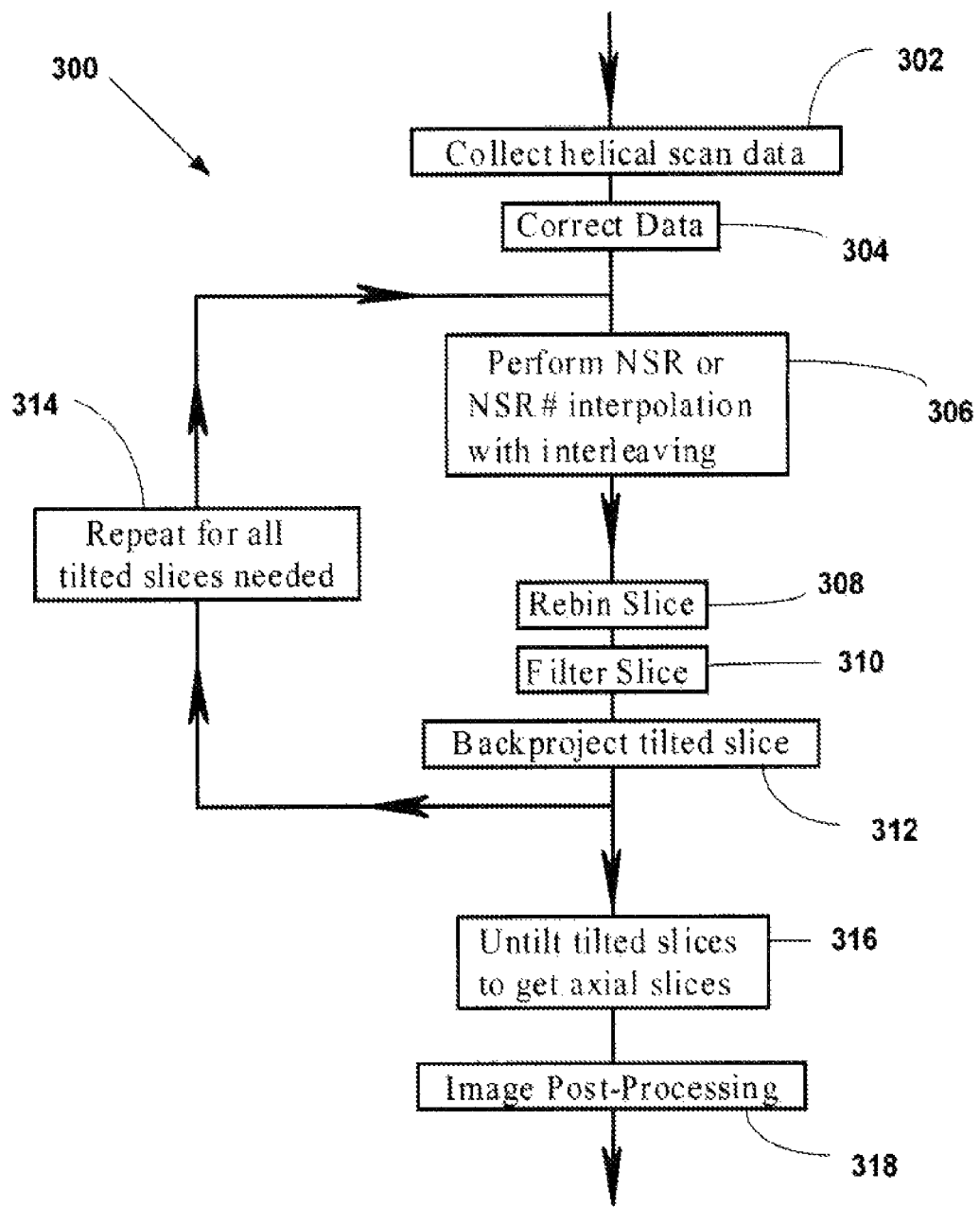
FIG. 7 is a flow chart of the steps taken in accordance in accordance with one embodiment of the NSR# method.

One embodiment of an implementation of a NSR# algorithm is illustrated in FIG. 7. The flow chart of FIG. 7 includes steps of a method configured and arranged to be carried out on a CT helical scanner designed to include a quarter detector offset in a multi-slice helical geometry (such as shown in FIGS. 1-3 and in FIG. 4). In one embodiment the NSR# algorithm is derived by modifying the NSR and AMPR algorithm framework to adjust the tilt angle of the tilted planes used in 2D reconstruction in a specific way to achieve complementary samples which are interleaved to achieve higher in-plane sampling rate.

In general, the NSR/AMPR algorithm is modified to create the NSR# algorithm so as to increase the in-plane resolution of the NSR/AMPR reconstruction algorithm. The NSR# as described herein varies from the NSR/AMPR algorithm in the following ways:

(A) Data are interleaved before reconstruction into tilted planes;

(B) The data chosen to be interleaved are different from the ones used in the traditional NSR/AMPR algorithm (different angle δ);

(C) To reduce artifacts non-interleaved (standard resolution) tilted images can be mixed with interleaved (high resolution) tilted images in the untilting process; and (D) The filtering used in the untilting process is different from the NSR/AMPR method The NSR# algorithm utilizes a unique technique in choosing the complementary data (angle δ) for interleaving. One embodiment of the NSR# technique includes the following steps shown in FIG. 7 at 300:

First, helical scan data with a given pitch is collected at step 302. At step 304, the data is correct for offset, log, air, monitor, spectral and other necessary corrections as given by protocol. Next step 306 is performed, whereby NSR# interpolation so as to calculate data that lie in a tilted image plane and interleaving is performed with the complementary data in accordance with the NSR# algorithm. At step 308, a rebinning interpolation is performed so as to convert data from a fan to a parallel domain. Filtering is performed at step 310, followed by back projecting the tilted slice at step 312. Step 314 proceeds to repeat steps 306-312 until all of the tilted slices that are requested are created. Once that occurs, process proceeds to step 316 so as to perform an untilted interpolation procedure so as to untilt the tilted slices to obtain axial slices. The process can then proceed to step 318 to perform image post processing.

As described, steps 302, 304, 308, 310, 312, 314 and 318 are substantially the same steps as performed the NSR/AMPR process. Steps 306 and 316 are however different.

As mentioned above in connection with FIG. 5, the tilted plane is obtained by starting with a plane 206 perpendicular to the z-axis, rotating the plane by angle γ about the Y-axis to plane 208 (plane 208 contains the Y-axis and forms an angle γ with respect to the X-axis), and rotate plane 208 about the X'-axis with angle δ to provide the plane 210 (plane 210 contains the X'-axis and forms an angle δ with respect to the Y-axis). In the NSR and NSR# algorithms the values of the angles γ and δ are predetermined for each tilted slice. Angle γ is determined by the scan pitch and is the same for all tilted planes, while angle δ is determined by the phase of the slice and the number of planes in an attachment point. The number of planes in an attachment point is predetermined for each possible scan pitch allowed for scanning. N is the number of fan views which are needed to reconstruct one tilted slice, α is the fan view angle defined with respect to the center of the tilted plane set of views, with the center view at θi.

Referring to the new step 306, for a helical scan of a given pitch the step includes the steps of:

(a) selecting the unique tilted plane data based on the angles $\gamma\#$ and $\delta\#$ (this will determine the NSR lines to be used for each tilted image);

(b) selecting the unique complementary tilted plane data based on the angles $\gamma_c\#$ and $\delta_c\#$ (this will determine the NSR lines to be used for each tilted image);

(c) performing a NSR interpolation; and (d) interleaving the complementary data.

As used in this step the angle $\gamma\#$ is solely determined by the scan pitch and is the same for all tilted planes. Note that $\gamma\#=\gamma_c\#=\gamma$ (the latter being used in the NSR/AMPR algorithm). However, the angle $\delta\#$ is determined by the phase of the slice and the number of planes in an attachment point. In this instance note that $\delta\#\neq\delta(\text{NSR/AMPR})$ and $\delta\#=-\delta_c\#$; or one of them is zero the other is $\pm\delta\#$. The number of planes in an attachment point is predetermined for each possible scan pitch allowed for scanning.

For the standard NSR/AMPR algorithm, the steps for the tilted plane i are as follows:

(a) compute the fan projection angle, α, with respect to the center of the tilted plane (θi); and (b) compute the NSR/AMPR interpolation equation as follows:

$$V_{\theta_i} = R_{sc}\sin\rho(\cos\alpha\tan\gamma\sec\delta + \tan\delta\sin\alpha) - \cos\rho(R_{sc}\tan\delta + S\alpha) \quad (1)$$

wherein Rsc is the source to iso-center distance,

ρ is the fan angle, and

S is the relative table displacement per one rotation of the scanner.

The next tilted plane (i+1) is computed using the above equation. However, the input data will be offset in view direction. Hence, the tilted plane for next slice will be numbered i+1 with center view at angle θi+Δθ.

Step 3 of the NSR# process is modified from the foregoing as follows: For tilted plane i, which uses data from the set of N views with center view at angle θi:

(a) the fan projection angle, α, is computed with respect to the center view of the tilted plane (θi);

(b) the NSR# interpolation equations are computed as follows with two data sets being obtained:

$$V_{\theta_i} = R_{sC}\sin\rho(\cos\alpha\tan\gamma\sec\delta + \tan\delta\sin\alpha) - \cos\rho(R_{sC}\tan\delta + l\alpha) \quad (2)$$

$$V_{\theta_i,-1} = R_{sC}\sin\rho(\cos\alpha\tan\gamma\sec(-\delta^\#) + \tan(-\delta^\#)\sin\alpha) - \cos\rho(R_{sC}\tan(-\delta^\#) + S\alpha) \quad (3)$$

$$V_{\theta_i,+1} = R_{sC}\sin\rho(\cos\alpha\tan\gamma\sec\delta^\# + \tan\delta^\#\sin\alpha) - \cos\rho(R_{sC}\tan\delta^\# + S\alpha) \quad (4)$$

Once computed, the algorithm moves 180° in view direction and NSR# equation (4) is applied to the tilted planes centered at (θi+π) and (θi−π).

Since the detectors of the detector array are arranged with a quarter detector offset, complementary data sets acquired 180° apart will be spatially interleaved so that the next step is to interleave the data sets as indicated by the following:

$$V_{\theta_i,-1} \text{ and } V_{\theta_i\pi,1} \text{ (These two data sets have the same z location.)} \quad (5)$$

$$V_{\theta_i,+1} \text{ and } V_{\theta_i-\pi,-1} \text{ (These two data sets have the same z location.)} \quad (6)$$

With respect to step 316 of FIG. 7, in the comparable step in the NSR/AMPR algorithm for a given pitch and a given axial slice thickness, the following can be observed: a number of tilted plane images are filtered in the z-direction with a trapezoidal filter of predetermined weights and width; the number of the tilted images used in the untilt to create one untilted (axial) image is determined from the portion of the images that lie inside the filter; and the untilt filter weights are inversely proportional to the z-distance of the tilted image point (x',y') from the axial image point (x,y).

Step 316 of FIG. 7 for the NSR# process is similar to this comparable step of the NSR/AMPR with the following exception: the user can reconstruct normal resolution planes using the NSR/AMPR algorithm in addition to the high resolution planes reconstructed using the NSR# algorithm; and the weights to be used for the normal resolution planes can be different from those used on the high resolution (NSR#) tilted planes, as requested by the imaging protocol or artifact—resolution balance needed.

Figure 8A:
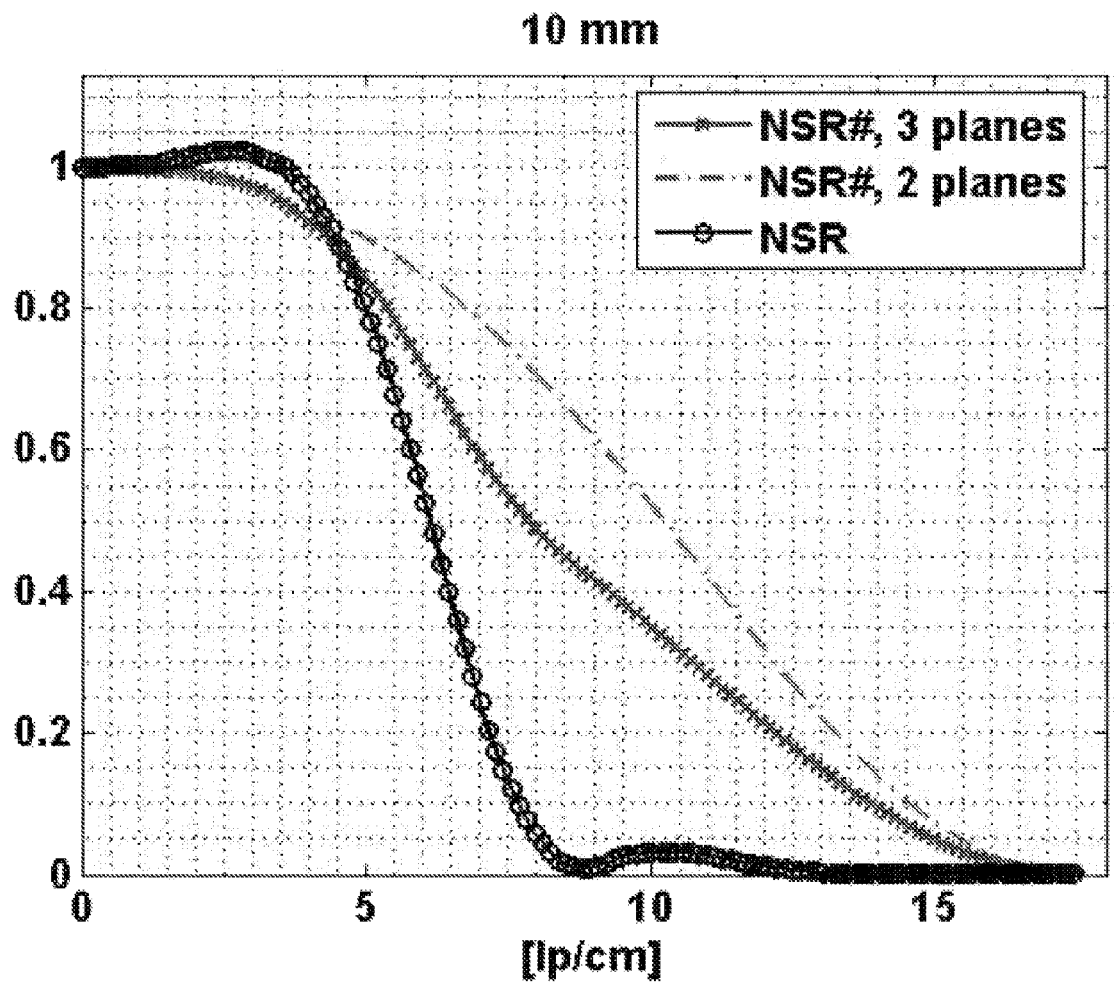
FIGS. 8A-8C are graphical illustrations of data generated with respect to a radial MTF on a scanner with a 17 lp/cm optical cutoff simulated at points located 10, 40 and 80 mm, respectively away from isocenter.
Figure 8B:
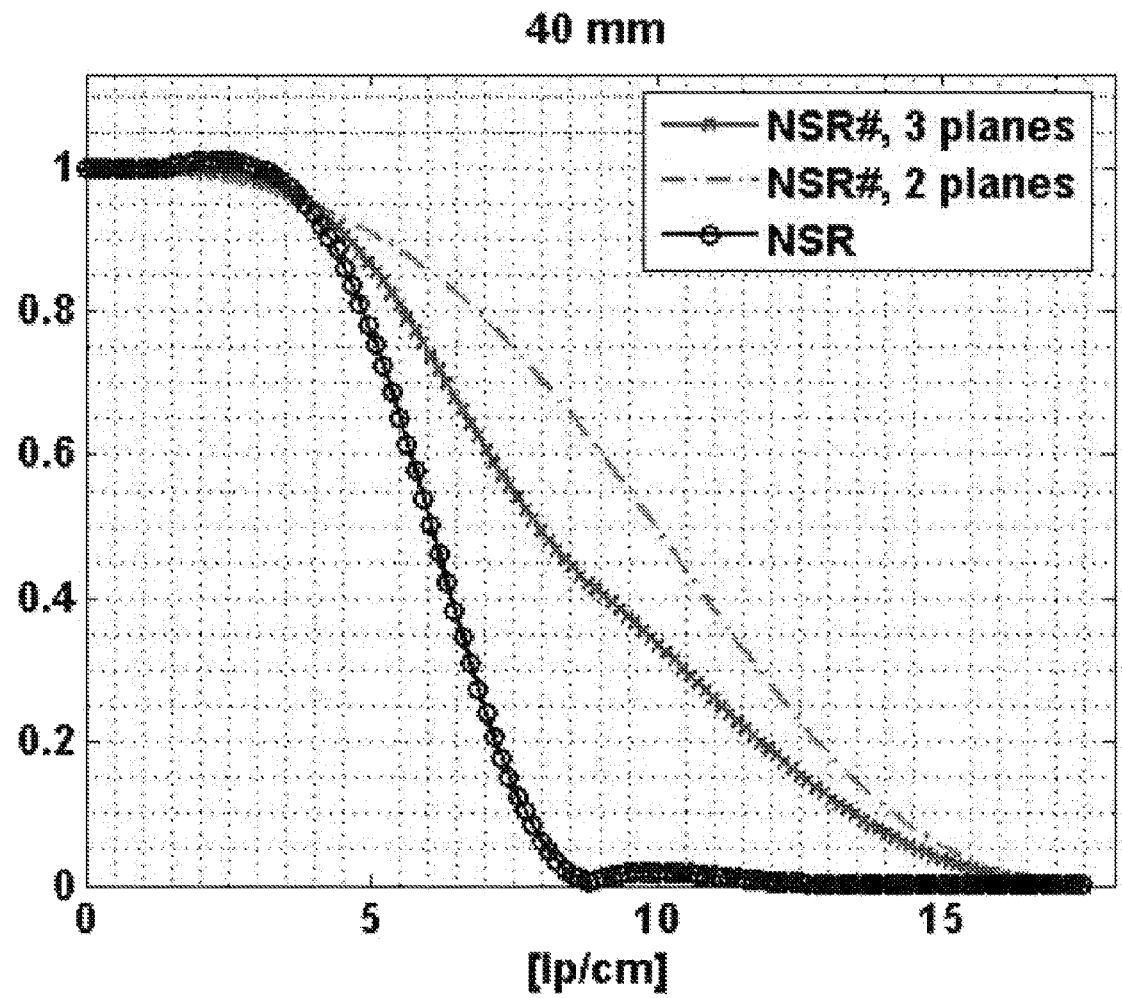
Figure 8C:
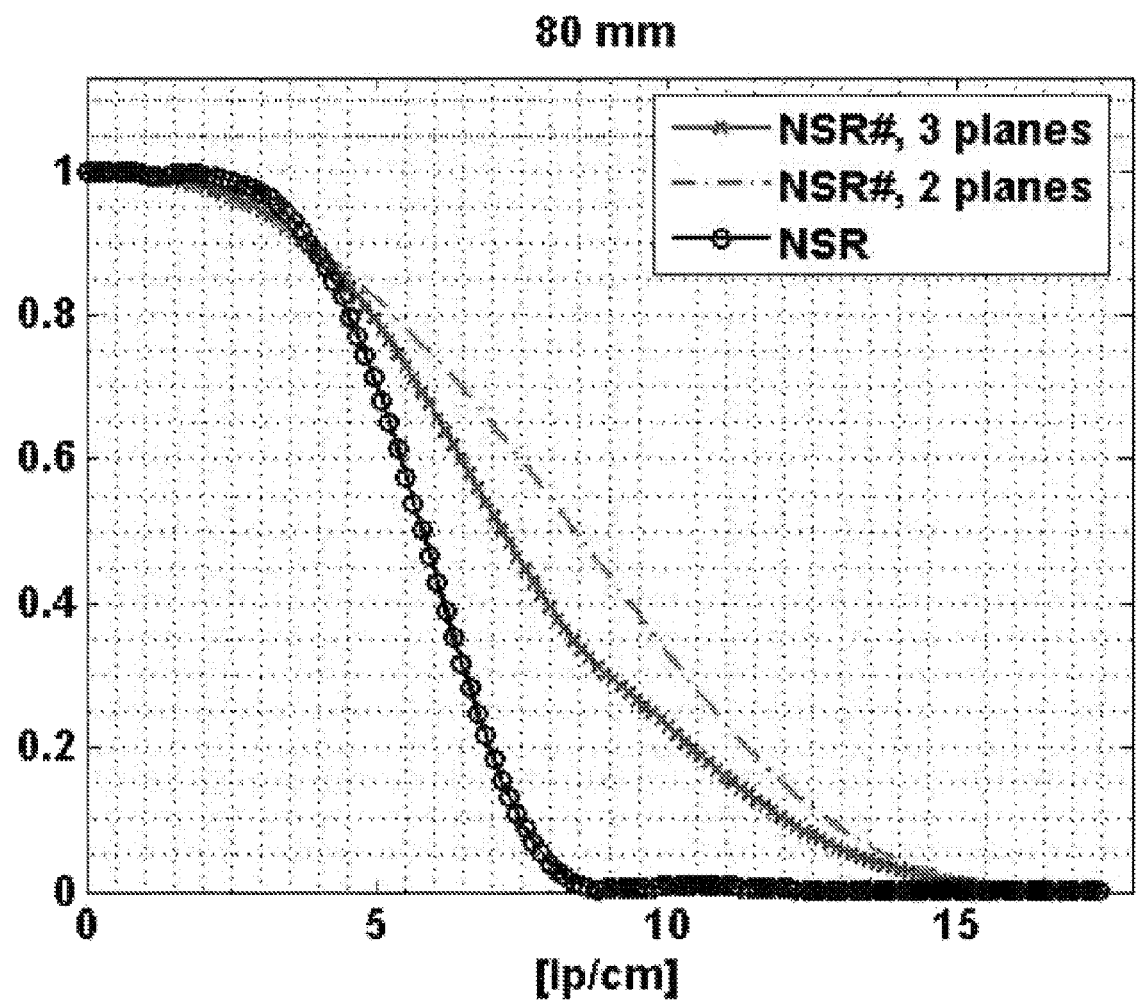

FIGS. 8A, 8B and 8C show the modulation transfer function of NSR# with 3 planes and NSR# with 2 planes, compared to the standard NSR algorithm. Helical pitch p=0.75. NSR is a prior art method, NSR# is the present invention.

Figure 9A:
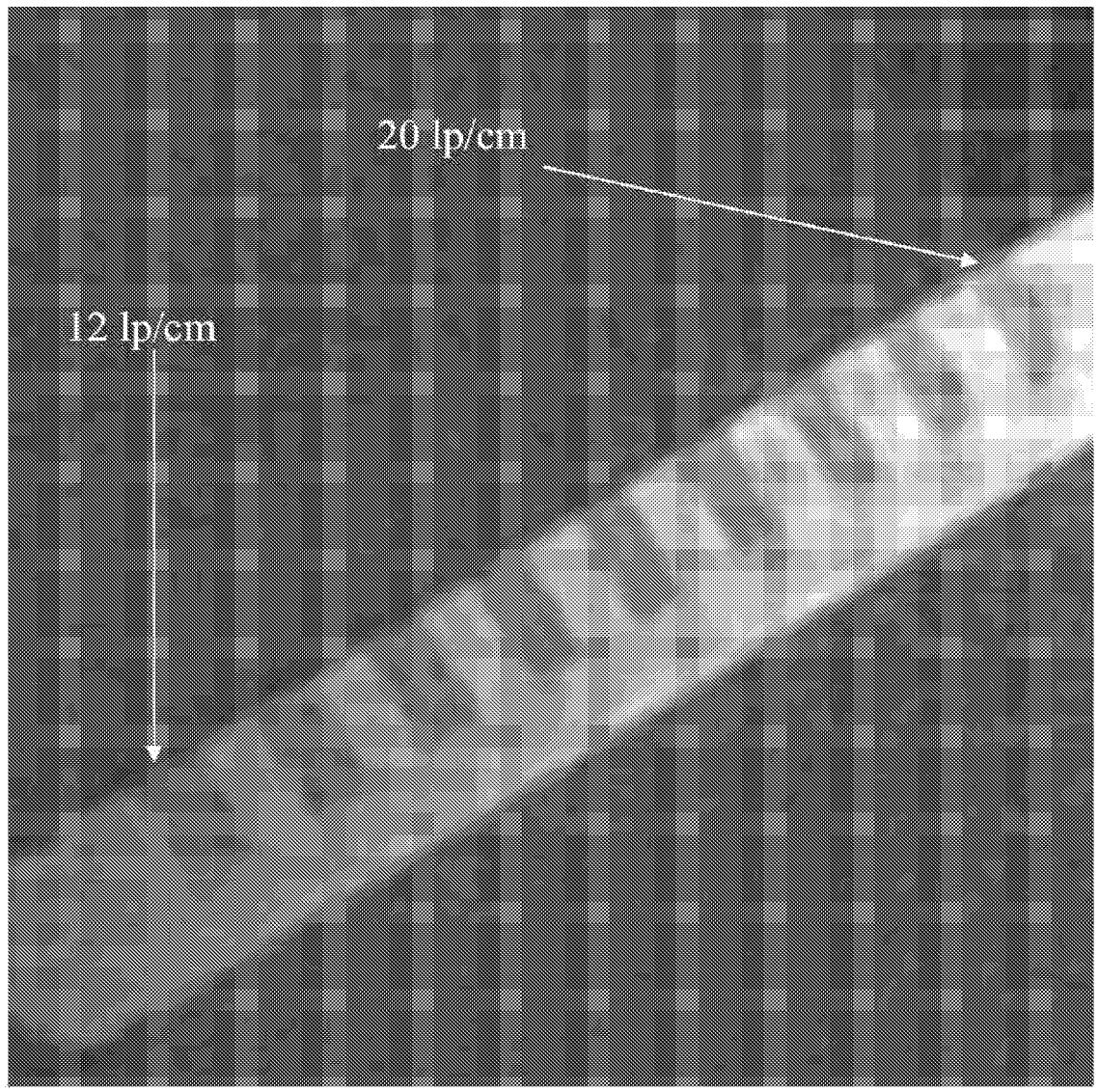
FIGS. 9A and 9B are images of a phantom section sold by Phantom Laboratory of Salem N.Y., USA, under the trademark and designation Catphan, CTP 446 using the NSR/AMPR process algorithm described herein.
Figure 9B:
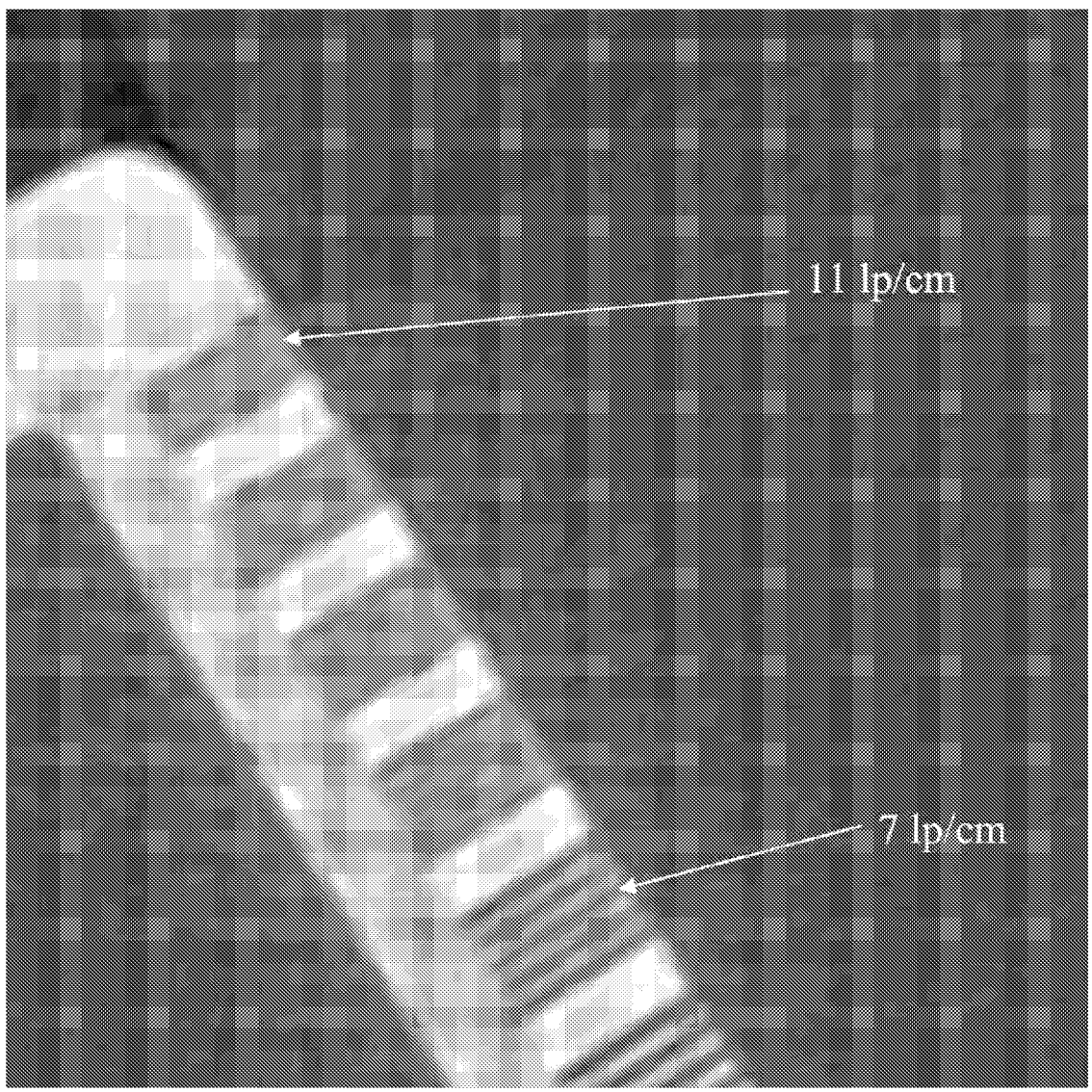
Figure 9C:
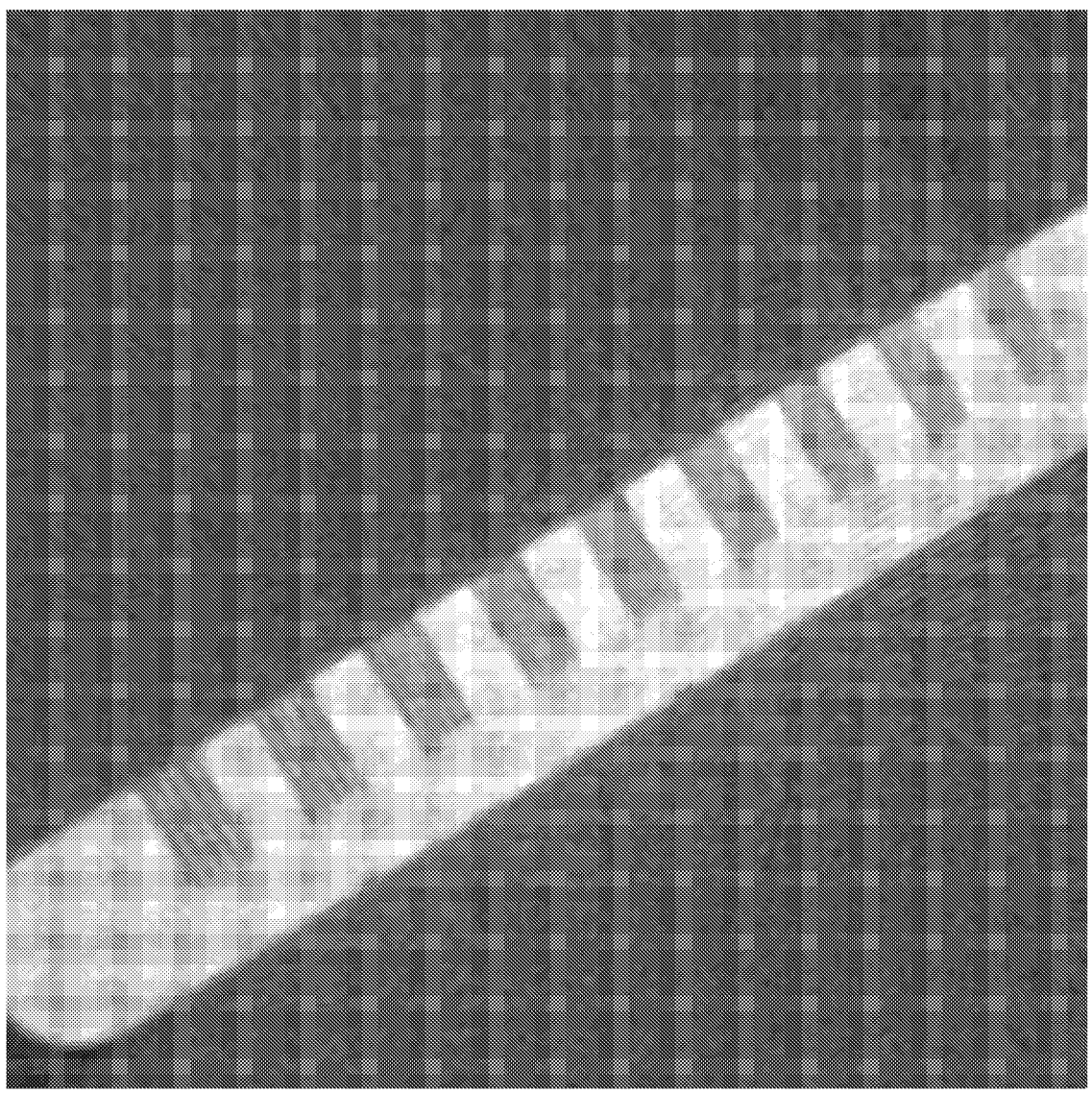
FIGS. 9C and 9D are images of the same Catphan CTP 446 phantom section generated using the NSR# process described herein in 3 planes for each section.
Figure 9D:
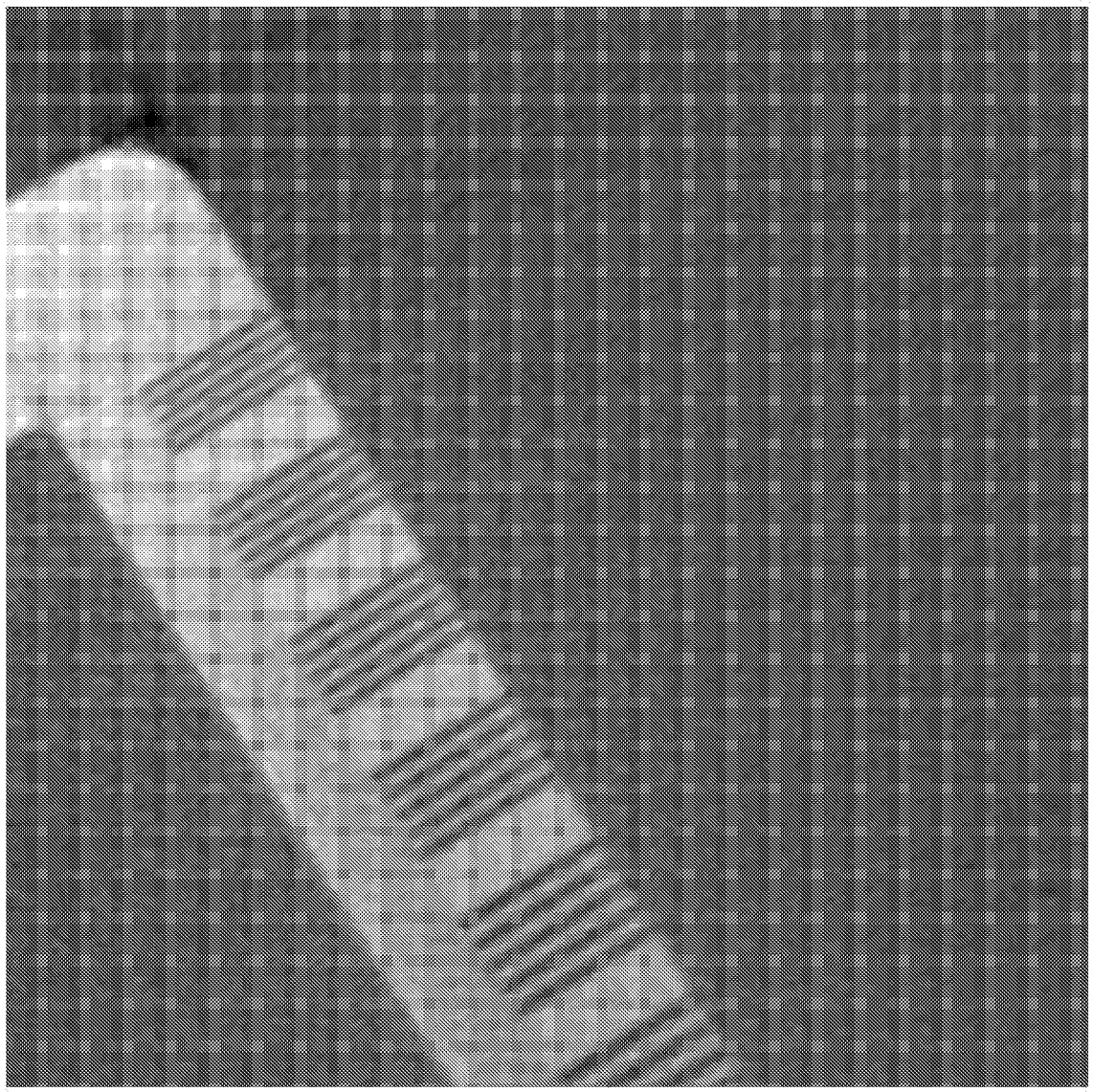
Figure 9E:
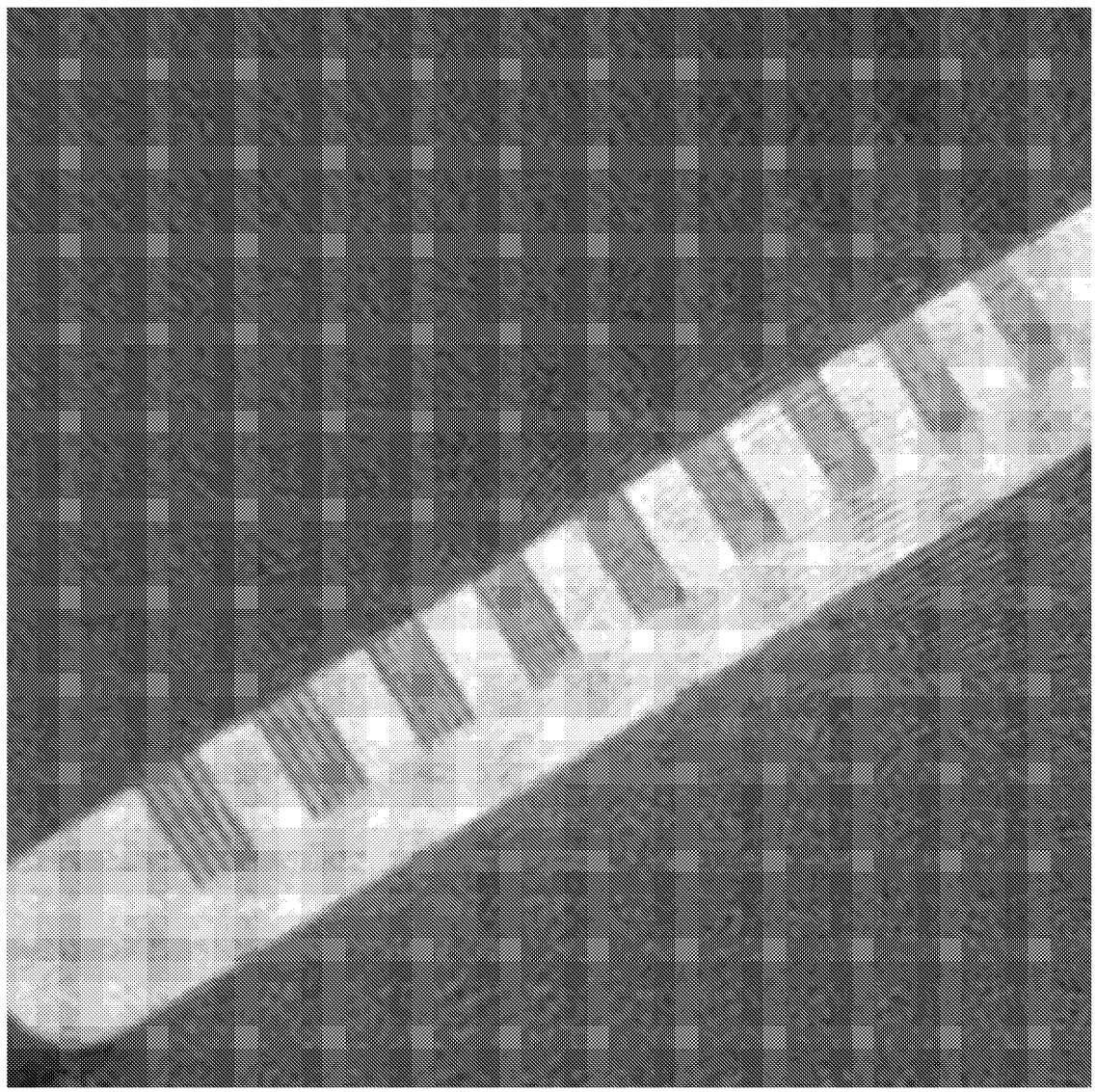
FIGS. 9E and 9F are images of the same image generated each using the NSR# process in 2 planes for each section.
Figure 9F:
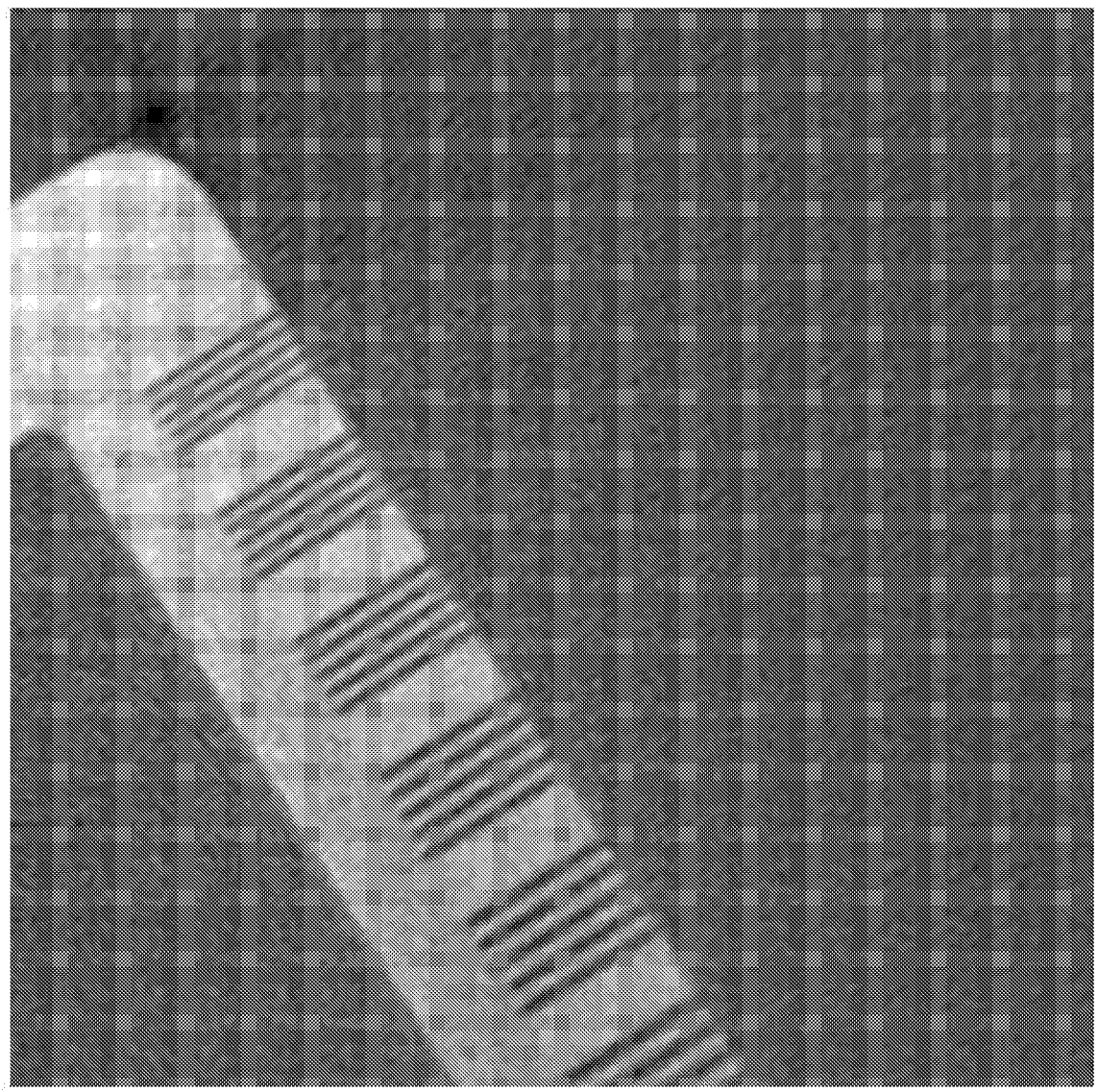

FIGS. 9A-9F show examples of images reconstructed from a helical scan of the high resolution comb section of a Catphan image quality phantom. One can see that the images generated using NSR# process with 2 planes (FIGS. 9E and 9F) has the higher resolution than the images generated using the NSR# process with 3 planes (FIGS. 9C and 9D), and the images generated using the NSR# process with 3 planes (FIGS. 9C and 9D) has higher resolution than standard NSR algorithm (FIGS. 9A and 9B). The NSR# process with 3 planes can be preferrable to the NSR# process with 2 planes in some protocols due to a lower degree of artifacts.

It should be evident that interleaving complementary data sets using the quarter detector offset results in an increase in in-plane resolution, while X-ray collimation provided in the scanner can be configured so as to decrease the amount of X-rays necessary for the scan so as to reduce the dose to the patient, in the part of the detector array that is not utilized. Further, the interleaved (high resolution) data can be filtered with a kernel and then reconstructed into high resolution tilted slices with respect to the rotation axis, wherein the non-interleaved data from the lower resolution planes are filtered with another kernel and then reconstructed into lower artifact tilted slices. The kernels used in the filtration of the non-interleaved data can be independent from the kernels used in the filtration of the interleaved data. The high resolution tilted slices and the low resolution tilted slices can be used to interpolate high resolution untilted images in planes perpendicular to the rotation axis.

In one embodiment the tilted planes are defined in sets of three planes, wherein two of the planes are complementary with attachment points 180° apart and δ of the complementary planes of the set is non-zero; wherein the third plane has an angle δ equal to zero. The data from the complementary pair can be used to interleave the data in the tilted plane, in order to increase the in-plane resolution. The data of the third plane with angle δ equal to zero are not interleaved. The interleaved data are filtered with a kernel and then reconstructed into high resolution tilted slices with respect to the rotation axis, wherein the data from the third plane are filtered with a kernel, independent from the above, and then reconstructed into lower artifact tilted slices. The high resolution tilted slices and the low artifact tilted slices are used to interpolate high resolution untilted images in planes perpendicular to the rotation axis.

Finally, two preferred embodiments of a method of generating a high resolution nutated slice reconstructed image of an object using a CT scanner in which the detectors are configured so as to provide a quarter detector offset will now be described.

Figure 10:
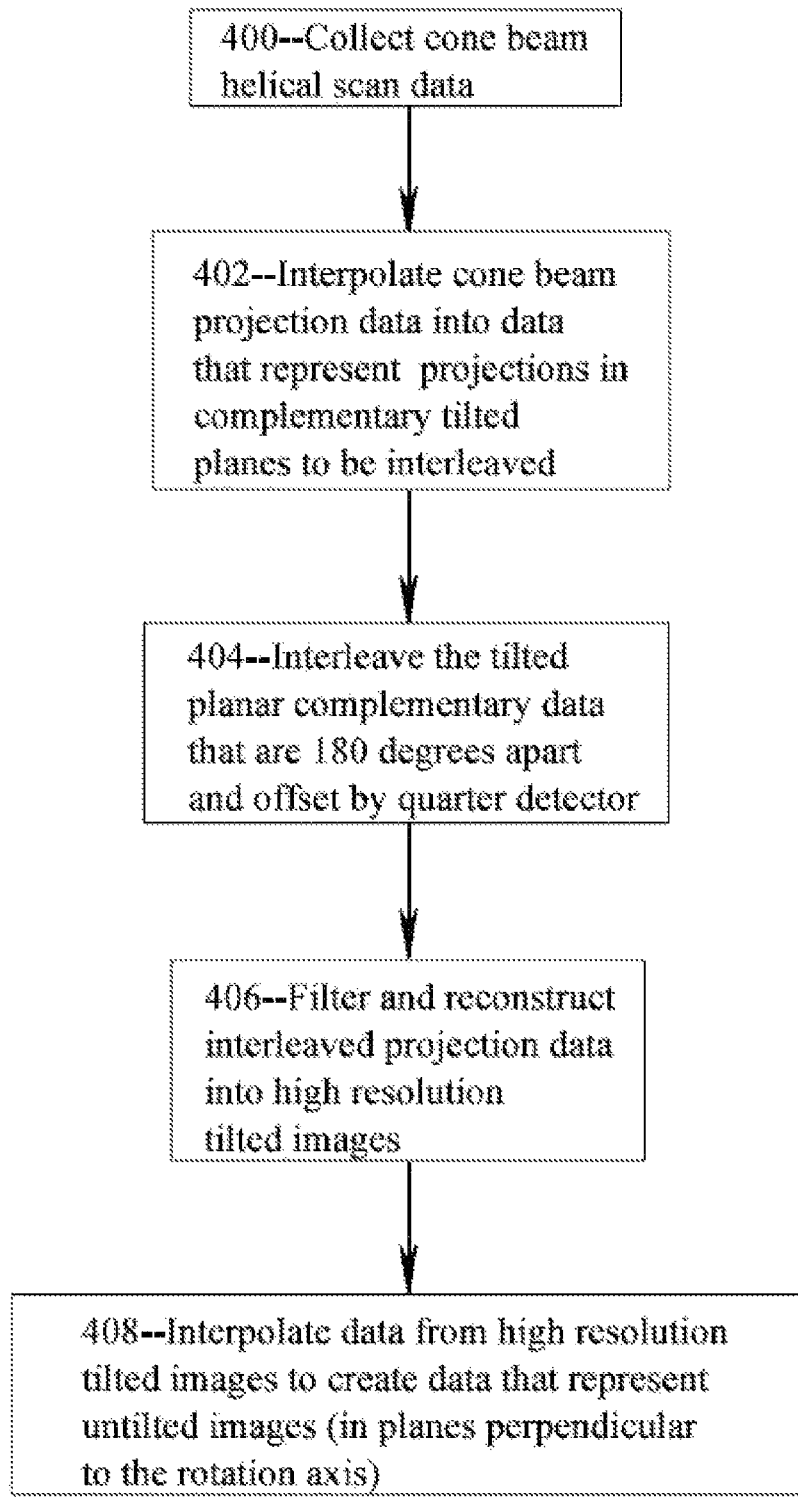
FIG. 10 shows a preferred method of generating a high resolution nutated slice reconstructed image of an object using a CT scanner in which the detectors are configured so as to provide a quarter detector offset will now be described.

Referring to FIG. 10, one embodiment comprises the following steps: First, at step 400 the object is scanned so as to generate helical cone beam projection data of the object using a fixed focal spot. At step 402 projection data for complementary high resolution tilted planes is interpolated from cone beam projection data. Then at step 404, tilted planar complementary projection data is interleaved utilizing the quarter detector offset. At step 406, the interleaved tilted planar projection data is filtered with a kernel and is then reconstructed for each of the planes so as to create high resolution tilted images. At step 408 data from the tilted images is interpolated so as to create data representing untilted images in planes perpendicular to the rotation axis.

Figure 11:
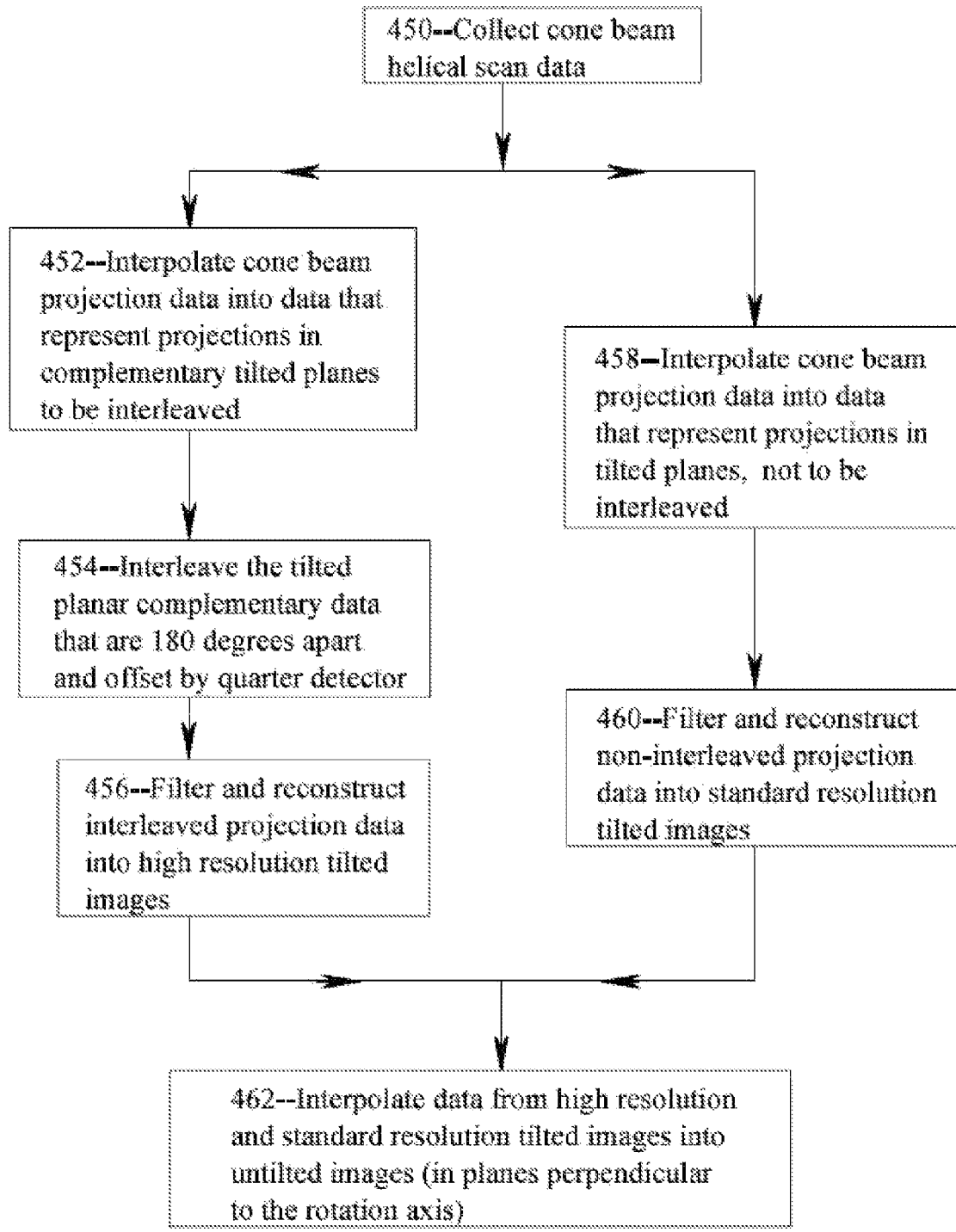
FIG. 11 shows another further preferred method of generating a high resolution nutated slice reconstructed image of an object using a CT scanner in which the detectors are configured so as to provide a quarter detector offset will now be described.

Referring to FIG. 11, a second embodiment comprises the following steps. First, at step 450 the object is scanned so as to generate helical cone beam projection data of the object using a fixed focal spot. At step 452, cone beam projection data to be used in reconstruction of high resolution tilted images is interpolated into data that represent projections that lie on complementary tilted planes to be interleaved. At step 454, tilted planar complementary projection data from complementary planes is interleaved utilizing the quarter detector offset. At step 456, the interleaved data is then filtered with a kernel and the interleaved projection data for each of the planes is reconstructed so as to create high resolution tilted images. In parallel, at step 458, cone beam projection data to be used in reconstruction of standard resolution tilted images is interpolated into tilted planar projection data. At step 460, non-interleaved projection data for standard resolution tilted planes is filtered with a separate kernel and reconstructed so as to create lower artifact standard resolution tilted images. At step 462, data from the high and standard resolution tilted images is then interpolated so as to create data representing image planes perpendicular to the rotation axis.

While this disclosure has been particularly shown and described with references to preferred embodiments thereof, it will be understood by those skilled in the art that various changes in form and details may be made therein without departing from the spirit and scope of the disclosure as defined by the following claims. In particular, with lower pitch scans one may use more tilted planes per attachment point. In the case, for example, where 5 tilted planes are determined per attachment point, the tilt angles delta are $-2\delta$, $-\delta$, 0, $+\delta$, and $+2\delta$. NSR# determines the planes with the tilt angles, $\delta_{-2}$#, $\delta_{-1}$#, 0, $\delta_{+1}$#, and $\delta_{+2}$#. These planes can be interleaved to create high resolution with the complementary plane from the 180 degree apart set of planes. The untilting process, as described above, may use only high resolution, interleaved tilted planes, or a mix of low artifact, non-interleaved planes, with high resolution tilted planes.

What is claimed is:

1. A helical CT scanner for scanning an object, comprising:
   an x-ray source constructed so as to define a focal spot, and
   a detector array comprising a plurality of detectors positioned to rotate with the source about an axis of rotation, wherein the source and detector array are arranged to rotate about a rotation axis with the object moving relative to and between the source and detector array in a direction parallel to the rotation axis during a helical scan; and
   a processor operative to process data acquired by the detector array during the helical scan, and based on the data, construct tilted slices with respect to the rotation axis, wherein each of the tilted slices are defined by an angle $\gamma$ with respect to the rotating X-axis and an angle $\delta$ with respect to the rotating Y-axis; wherein the angle $\gamma$ is chosen as a function of the pitch of the helical scan, so as to minimize the distance of the focal spot to the tilted slice for a center ray over all views used to reconstruct a tilted slice; wherein the angle $\delta$ is determined by the phase of the slice and a predetermined number of slices passing through each attachment point for each possible scan pitch; wherein the processor is further operative to interleave samples from pairs of complementary tilted slices to form combined slices, then reconstruct an image from each combined slice, and then untilt each image to form an untilted image that is perpendicular to the axis of rotation; wherein two tilted slices are complementary if they satisfy the following conditions: (1) respective attachment points of those tilted slices are separated by half a rotation of the x-ray source, and (2) planes intersect along a line which connects the two attachment points;
   wherein the x-ray source is constructed so as to define a fixed focal spot with respect to the detector array during the helical scan, and the detectors of the array are positioned relative to the source and axis of rotation during rotation so as to provide a quarter detector offset so that rays from 180° apart during rotation are interleaved.

2. A helical CT scanner according to claim 1, wherein the detector array comprises multiple rows of detectors.

3. A helical CT scanner according to claim 1, wherein a right handed stationary frame of reference, $X_s$, $Y_s$, $Z_s$, is defined and associated with the scanner, and a right handed rotating frame of reference X, Y, Z, is defined and rotates about the $Z_s$ axis so that the rotating Y axis is attached to the rotating x-ray focal spot, the Z axis is the same with the stationary $Z_s$ axis, and the X axis is perpendicular to both Y and Z, so that it forms a right handed frame of reference.

4. A helical CT scanner according to claim 1, wherein multiple slices are defined in groups so that all of the slices of the same group have a common attachment point spatially attached at the focal spot on the rotating Y-axis of the scanner;
   wherein all slices of the same group have the same angle $\gamma$;
   wherein all slices of the same group have a different angle $\delta$.

5. A helical CT scanner according to claim 1, wherein the process is further operative to, based on the reconstructed images, to interpolate high resolution untilted images in planes perpendicular to the rotation axis.

6. A helical CT scanner according to claim 1, wherein the angles $\delta$ of both of the tilted planes of the complementary pair are non-zero.

7. A helical CT scanner according to claim 1, wherein the angles $\delta$ of both of the tilted planes of the complementary pair have opposite signs.

8. A helical CT scanner according to claim 1, wherein the angle $\delta$ of one of the tilted planes of each complementary pair is zero and the angle $\delta$ of the other tilted plane of each complementary set is non-zero.

9. A helical CT scanner according to claim 4, wherein the pitch of the helical scan is less than $2/3$.

10. A helical CT scanner according to claim 4, wherein the processor defines the tilted planes in sets of three or more planes;
   wherein two of the tilted planes are complementary with attachment points 180° apart and the angle $\delta$ of the complementary planes of the set is non-zero;

wherein the rest of the planes are not interleaved and have an angle δ that is zero or non-zero.

11. A helical CT scanner according to claim 1, wherein the processor is further operative to filter interleaved data with a first kernel so that filtered data are reconstructed into high resolution tilted slices with respect to the rotation axis, and to filter non-interleaved data with a second kernel so that the filtered data provided by the second kernel are reconstructed into lower artifact tilted slices.

12. A helical CT scanner according to claim 11, wherein the first and second kernels are independent of one another.

13. A helical CT scanner according to claim 12, wherein the high resolution tilted slices and the low artifact tilted slices are used to interpolate high resolution untilted images in planes perpendicular to the rotation axis.

14. A helical CT scanner according to claim 4, herein the tilted planes are defined in sets of three planes;
wherein two of the planes are complementary with attachment points 180° apart and the angle δ of the complementary planes of the set is non-zero;
wherein the third plane has an angle δ equal to zero.

15. A method of generating a high resolution nutated slice reconstructed image of an object with a CT scanner comprising a x-ray source constructed so as to define a fixed focal spot, and a detector array comprising a plurality of detectors positioned to rotate with the source about an axis of rotation and arranged to as to provide a quarter detector offset, wherein the source and detector array are arranged to rotate about a rotation axis with the object moving relative to and between the source and detector array in a direction parallel to the rotation axis during a helical scan, the method comprising:
scanning the object so as to generate helical scan projection data of the object using a fixed focal spot;
creating data for selected tilted planes to be interleaved; wherein each of the tilted planes are defined by an angle γ with respect to the rotating X-axis and an angle δ with respect to the rotating Y-axis; wherein the angle γ is chosen as a function of the pitch of the helical scan, so as to minimize the distance of the focal spot to the tilted plane for a center ray over all views used to reconstruct a tilted plane; wherein the angle δ is determined by the phase of the plane and a predetermined number of planes passing through each attachment point for each possible scan pitch;
interleaving samples from pairs of complementary tilted planes to form combined planes, wherein two tilted planes are complementary if they satisfy the following conditions: (1) respective attachment points of those tilted planes are separated by half a rotation of the x-ray source, and (2) the planes intersect along a line which connects the two attachment points;
filtering with the combined planes with a kernel;
reconstructing images from the combined planes so as to create high resolution tilted images; and
interpolating data from the tilted images, creating untilted images in planes perpendicular to the rotation axis.

* * * * *